United States Patent
Marsh et al.

(10) Patent No.: US 10,850,043 B2
(45) Date of Patent: Dec. 1, 2020

(54) INJECTION DEVICE

(71) Applicant: Sanofi, Paris (FR)

(72) Inventors: William Marsh, Warwickshire (GB); Anthony Paul Morris, Coventry (GB); Joseph Butler, Rugby (GB); Matthew Jones, Warwick (GB)

(73) Assignee: Sanofi, Paris (FR)

( * ) Notice: Subject to any disclaimer, the term of this patent is extended or adjusted under 35 U.S.C. 154(b) by 145 days.

(21) Appl. No.: 16/017,794

(22) Filed: Jun. 25, 2018

(65) Prior Publication Data

US 2018/0304027 A1 Oct. 25, 2018

Related U.S. Application Data

(63) Continuation of application No. 14/783,121, filed as application No. PCT/EP2014/057004 on Apr. 8, 2014, now Pat. No. 10,004,852.

(30) Foreign Application Priority Data

Apr. 10, 2013 (EP) .................................... 13163113

(51) Int. Cl.
*A61M 5/31* (2006.01)
*A61M 5/315* (2006.01)
(Continued)

(52) U.S. Cl.
CPC .......... *A61M 5/31583* (2013.01); *A61M 5/20* (2013.01); *A61M 5/3155* (2013.01);
(Continued)

(58) Field of Classification Search
CPC ............ A61M 5/31583; A61M 5/3155; A61M 5/3157; A61M 5/31553; A61M 5/31561;
(Continued)

(56) References Cited

U.S. PATENT DOCUMENTS 5,961,495 A 10/1999 Walters et al.
6,004,297 A 12/1999 Steenfeldt-Jensen et al.
(Continued)

FOREIGN PATENT DOCUMENTS

CN 103128025 6/2013
DE 3645245 1/1994
(Continued)

OTHER PUBLICATIONS

International Preliminary Report on Patentability in International Application No. PCT/EP2014/057004, dated Oct. 13, 2015, 14 pages.
(Continued)

*Primary Examiner* — Amber R Stiles
(74) *Attorney, Agent, or Firm* — Fish & Richardson P.C.

(57) ABSTRACT

The disclosure refers to a handheld injection device comprising a housing, a dose indicator positioned within and axially constrained to the housing and rotatable with respect to the housing during dose setting and during dose dispensing, a gauge element, which is at least partly interposed between the housing and the dose indicator, wherein the gauge element is axially guided within the housing and in threaded engagement with the dose indicator such that rotation of the dose indicator causes an axial displacement of the gauge element (80; 490). A contrast element having a first marking is provided and at least a region of the gauge element is provided with a second marking, with the first marking and/or the second marking being visible through a first window or aperture in the housing depending on the axial position of the gauge element within the housing.

18 Claims, 6 Drawing Sheets

(51) Int. Cl.
*A61M 5/20* (2006.01)
*A61M 5/24* (2006.01)

(52) U.S. Cl.
CPC ...... *A61M 5/3157* (2013.01); *A61M 5/31553* (2013.01); *A61M 5/31561* (2013.01); *A61M 5/24* (2013.01); *A61M 5/31541* (2013.01); *A61M 5/31568* (2013.01); *A61M 2005/3125* (2013.01); *A61M 2005/3126* (2013.01); *A61M 2205/581* (2013.01); *A61M 2205/582* (2013.01); *A61M 2205/583* (2013.01)

(58) Field of Classification Search
CPC ............ A61M 5/20; A61M 2005/3126; A61M 2205/581; A61M 5/31568; A61M 2205/582; A61M 2205/583; A61M 5/31541; A61M 5/24; A61M 2005/3125
See application file for complete search history.

(56) References Cited

U.S. PATENT DOCUMENTS

| | | | |
|---|---|---|---|
| 6,228,067 | B1 | 5/2001 | Gabriel |
| 6,899,699 | B2 | 5/2005 | Enggaard |
| 7,427,275 | B2 | 9/2008 | DeRuntz et al. |
| 8,096,978 | B2 | 1/2012 | Markussen |
| 2007/0129687 | A1 | 6/2007 | Marshall et al. |
| 2008/0269688 | A1 | 10/2008 | Colucci et al. |
| 2008/0306445 | A1 | 12/2008 | Burren et al. |
| 2008/0306446 | A1 | 12/2008 | Markussen |
| 2009/0048561 | A1 | 2/2009 | Burren et al. |
| 2010/0168677 | A1* | 7/2010 | Gabriel .............. A61M 5/31585 604/189 |
| 2010/0228195 | A1 | 9/2010 | Ulrich et al. |
| 2011/0004166 | A1 | 1/2011 | Wittmann et al. |
| 2011/0054412 | A1 | 3/2011 | Eich et al. |

FOREIGN PATENT DOCUMENTS

| | | |
|---|---|---|
| DE | 29703820 | 7/1998 |
| DE | 10232412 | 2/2004 |
| DE | 69629391 | 6/2004 |
| DE | 20317377 | 3/2005 |
| DE | 102005008280 | 7/2006 |
| DE | 102005063311 | 8/2006 |
| DE | 102005044096 | 11/2006 |
| DE | 102005023824 | 12/2006 |
| DE | 102005060929 | 3/2007 |
| DE | 202008011175 | 1/2010 |
| DE | 202009003050 | 8/2010 |
| EP | 0762904 | 3/1997 |
| EP | 1304129 | 4/2003 |
| EP | 1669028 | 6/2006 |
| EP | 1804858 | 10/2009 |
| RU | 2401134 | 10/2010 |
| WO | WO 95/32749 | 12/1995 |
| WO | WO 98/39041 | 9/1998 |
| WO | WO 2000/041754 | 7/2000 |
| WO | WO 2004/078241 | 9/2004 |
| WO | WO 2005/046770 | 5/2005 |
| WO | WO 2006/040296 | 4/2006 |
| WO | WO 2006/045528 | 5/2006 |
| WO | WO 2008/116766 | 10/2008 |
| WO | WO 2008/145171 | 12/2008 |
| WO | WO 2008/148864 | 12/2008 |
| WO | WO 2009/125879 | 10/2009 |
| WO | WO 2010/020311 | 2/2010 |
| WO | WO 2010/056367 | 5/2010 |
| WO | WO 2011/010764 | 1/2011 |
| WO | WO 2011/060785 | 5/2011 |
| WO | WO 2011/068531 | 6/2011 |
| WO | WO 2011/101349 | 8/2011 |
| WO | WO 2013/110538 | 8/2013 |

OTHER PUBLICATIONS

International Search Report and Written Opinion in International Application No. PCT/EP2014/057004, dated Nov. 18, 2014, 19 pages.
Rote Liste, "50. Hypophysen-, Hypothalamushormone, andere regulatorische Peptide u. ihre Hemmstoffe," Chapter 50, ed. 2008, 20 pages.
International Preliminary Report on Patentability in International Application No. PCT/EP2014/068601, dated Mar. 8, 2016, 6 pages.
International Search Report and Written Opinion in International Application No. PCT/EP2014/068601, dated Sep. 17, 2014, 9 pages.
Pen-injectors for medical use—Part 1: Pen-injectors—Requirements and test methods, International Standard, reference No. ISO 11608-1 :2000(E), first edition Dec. 15, 2000, 32 pages.

* cited by examiner

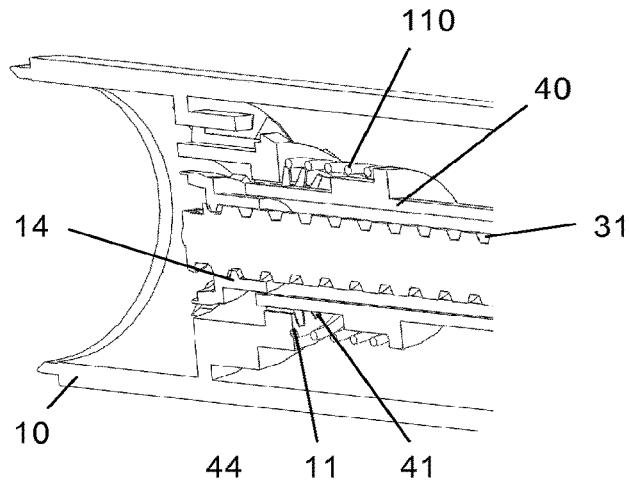
Figure 8
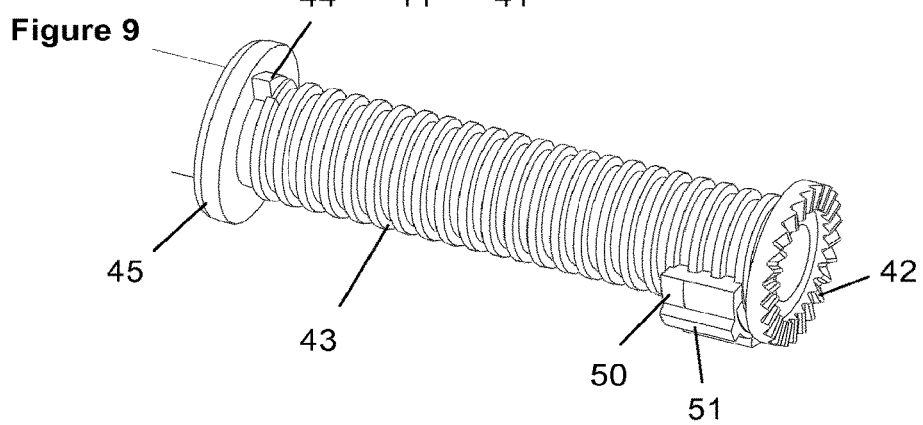
Figure 9
Figure 10
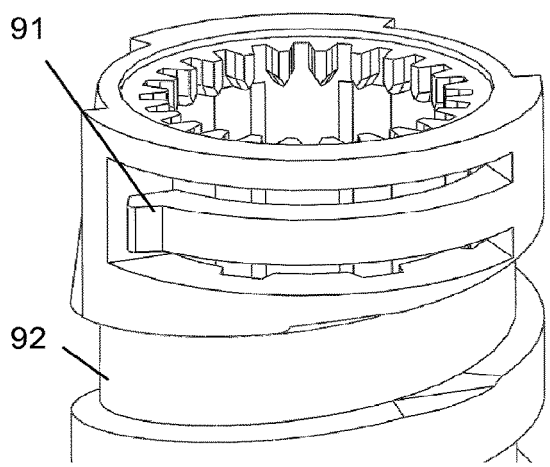
Figure 11
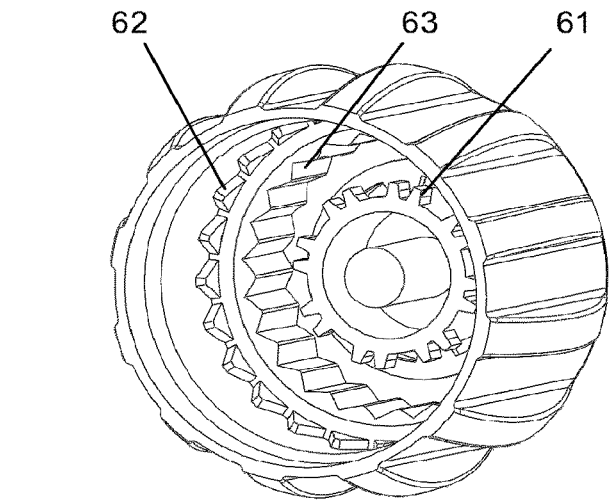

INJECTION DEVICE

CROSS-REFERENCE TO RELATED APPLICATIONS

This application is a continuation of U.S. patent application Ser. No. 14/783,121, filed Oct. 8, 2015, which is a U.S. national stage application under 35 USC § 371 of International Application No. PCT/EP2014/057004, filed on Apr. 8, 2014, which claims priority to European Patent Application No. 13163113.7, filed on Apr. 10, 2013, the entire contents of which are incorporated herein by reference.

TECHNICAL FIELD

The present disclosure is generally directed to a handheld injection device, i.e. a drug delivery device for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. In general, the present disclosure is applicable for all of these types of devices, i.e. for devices with or without a drive spring.

These types of pen delivery devices (so named because they often resemble an enlarged fountain pen) generally comprise of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A disposable drug delivery device for selecting and dispensing a number of user variable doses of a medicament according to the present disclosure typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. The remaining dose in the cartridge is indicated to the user by the position of the bung and the distal end of the piston rod within the cartridge. Especially visually impaired users may find it difficult to identify the remaining dose in the cartridge.

EP 1 804 858 B1 discloses an injection device which comprises a housing, a resilient member and a dose setting member operatively connected to a dose indicator barrel positioned within the housing. The resilient member is a helical spring adapted to provide a force in the axial direction of the injection device, the force being necessary for ejecting a dose from the injection device. The dose setting member and the dose indicator barrel are movable relative to each other and cooperate to set the dose to be ejected from the injection device. The dose indicator barrel engages a threaded portion of the housing. The dose indicator barrel, during dose setting, is adapted undergo a combined rotational and translational movement within the housing and relative to the housing. The combined rotational and translational movement of the dose indicator barrel is caused by its threaded interface with the housing. Generally, a translational movement of a dose indicator barrel during dose setting either results in the indicator barrel protruding from the housing depending on the amount of the set dose or this requires a relatively long housing, if it is preferred that the barrel is covered within the housing independent of the set dose.

U.S. Pat. No. 8,096,978 B2 discloses an injection device comprising a housing, a rotatable dose setting member, a power reservoir, a release member, a piston rod and a rotatably arranged drive member. The drive member is positionable in two different axial positions, which are a first (dose setting) position, when the dose setting member is in its dose setting position, and a second (injection) position, when the dose setting member is in its injection position. Further, the dose setting member is positionable in two different axial positions for dose setting and injection, respectively. Although the drive member is allowed to move axially relative to the piston rod, the axial movement of the drive member bears the risk of the drive member entraining the piston rod which might result in a dose inaccuracy.

Further, WO 2008/145171 A1 describes an injection device where the force necessary for ejecting a dose from the injection device is established manually, i.e. without the aid of a spring or the like. This device comprises a housing, a first component for pressing out the injection liquid from a container and a dosing component in threaded engagement with the first component. The dosing component can rotate together with the first component relative to the housing for the purpose of selecting a desired injection dosing. Further, the dosing component is in threaded engagement with a window sleeve which moves axially within the housing and relative to the dosing component upon rotation of the dosing component. The window sleeve is axially guided within a slot of the housing, wherein the length of the window sleeve is such that the slot is at any position of the window sleeve closed by the window sleeve. A number scale provided on the dosing component is visible through an aperture in this window sleeve. A knob is provided, which is rotated during dose setting and which is simultaneously axially moved away from the housing as the window sleeve translates out of the housing during dose setting. Thus, although the dosing component does not perform a translational movement during dose setting, there is still a component (knob with window sleeve) protruding from the housing when a dose is set.

SUMMARY

In some aspects, a drug delivery device is provided with an improved dose display. The drug delivery device can be compact in size, preferably without components translating out of the housing during dose setting.

According to a first embodiment, the handheld injection device comprises a housing, a dose indicator, a gauge element and a contrast element. The dose indicator may be split into two parts for moulding reasons, but they are rigidly fixed together during assembly so that they function as a single part. The dose indicator is preferably positioned within and axially constrained to the housing and rotatable with respect to the housing during dose setting and during dose dispensing. The gauge element may be at least partly interposed between the housing and the dose indicator. Preferably, the gauge element is axially guided within the housing and in threaded engagement with the dose indicator such that rotation of the dose indicator causes an axial displacement of the gauge element. If the contrast element has a first marking and at least a region of the gauge element has a second marking, either only the first marking or only the second marking or both markings are visible through a first window or aperture in the housing depending on the axial position of the gauge element within the housing. In other words, the gauge element may screen or uncover the contrast element as the gauge element travels axially within the housing. Preferably, the region of the gauge element having the second marking is interposed between the housing and the contrast element. This provides an analogue optical dose set and dispense feedback to the user.

This visual feedback feature, which is preferably provided in addition to a number display (for example provided by the dose indicator), gives clear feedback to the user regarding the approximate size of the dose set. The dispense speed of a spring driven injector mechanism may be higher than for a manual injector device, so it may not be possible to read the typical numerical dose display during dispense. The gauge feature provides feedback to the user during dispense regarding dispense progress without the need to read the dose number itself. In addition, this gauge display simulates a syringe action during dose set and dispense.

As an alternative to the gauge element having the marking and being visible through the aperture or window of the housing, this could be formed using a separate component engaged with the dose indicator, for example on a different helical track.

The device may have the typical pen shape with at least most of the component parts being arranged concentrically about a longitudinal axis of the device. As an alternative, a piston rod may define a first longitudinal axis and dose setting means may be rotatable about a second longitudinal axis. In this alternative, the first longitudinal axis is spaced from the second longitudinal axis, i.e. there is an offset between the two axes on which the component parts of the device are arranged. Preferably, the first longitudinal axis is parallel to the second longitudinal axis. As an alternative, the two axes may be tapered, but still with an offset between the axes within the device. Due to some of the component parts being located next to others instead of the conventional concentrically arrangement, the cross-section of the device becomes rather elongated than the usual circular pen-shape. This improves handling of the device at least for some users. Further, the device may be made shorter, which again improves handling and convenience. Providing the power reservoir for driving the driver reduces the force required for the user during dose dispensing. This is especially helpful for users with impaired dexterity.

Preferably, the gauge element is interposed between the housing and the dose indicator such that at least a part of the gauge element is arranged within the housing and that it is surrounding or shielding at least a part of the dose indicator. For example, the gauge element is essentially fully contained within the housing and may travel axially within the housing overlapping a smaller or larger part of the dose indicator depending on the axial position of the gauge element.

Generally, the two markings provided on the gauge element and on the contrast element, respectively, may be any visually distinguishable different appearance of the two elements, thus allowing a user to at least roughly identify the different axial positions of the gauge element within the housing. For example, the marking on the gauge element may be formed by an opaque sliding element revealing the contrast element, which may be a contrasting coloured component underneath. Alternatively, the concealed component may be printed with coarse dose numbers or other indices to provide more precise resolution.

It is preferred if the contrast element is axially constrained to the housing. For example the contrast element may be unitary with the housing or with the dose indicator.

In a preferred embodiment, there is only one window in the housing, showing both the gauge area that covers and reveals the contrast element and also showing the dose number on the dose indicator. If the housing has a second aperture or window and the gauge element has a third aperture or window, these two further apertures or windows may be positioned with respect to each other such that at least a part of the dose indicator is visible through the second and third apertures or windows. The dose indicator may be marked with a sequence of numbers or symbols. With the dose indicator (number sleeve) located radially inwards of the gauge element, this allows that at least one of the numbers or symbols on the dose indicator is visible through the apertures or windows. In other words, the gauge element may be used to shield or cover a portion of the dose indicator and to allow view only on a limited portion of the dose indicator. This function of a precise dose indication may be in addition to the gauge element itself being suitable for identifying or indicating the actually set and/or dispensed dose as mentioned above.

Preferably, with the exception of the apertures or windows the gauge element is fully concealed within the housing, irrespective of its axial position relative to the housing. In other words, the gauge element does not protrude out of the housing during dose setting and during dose dispensing. This makes the device compact in use and improves its handling.

To avoid that the gauge element protrudes out of the housing during dose setting and during dose dispensing, the gauge element may be guided in the housing such that the gauge element at least in one of its axial positions during dose setting overlaps at least a part of a cartridge, which might be retained in a cartridge holder.

According to a preferred embodiment, the injection device further comprises a resilient member adapted to provide a force necessary for ejecting a dose from the injection device. The resilient member (power reservoir) is preferably a torsion spring. Such a torsion spring may be strained during dose setting. The spring is preferably pre-loaded and is further strained by the user during dose setting. The stored energy is at least in part released during dose dispensing.

As an alternative, the spring may be fully pre-charged for the expected life of the device, (reducing the effort required to use the device) i.e. such that a user is not required to re-charge or strain the spring at any time. Suitable spring types include compression springs and torsion springs. According to some embodiments, the spring is a reverse wound flat spiral spring, which is a band-type spring which is wound up in its charged state counter to its unstressed winding direction. Preferably, a first end of the spring is attached to a first spool, which may be located on a first longitudinal axis, and a second end of the spring is attached to a second spool, which may be located on a second longitudinal axis. For driving the driver, one of the spools may be coupled to the driver, e.g. by means of a direct splined coupling. As an alternative, a releasable coupling may be used, e.g. a pair of teeth rings.

Dose dispensing may be effected by the use of a piston rod acting on a bung in the cartridge. Preferably, the piston rod does not rotate during dose setting and rotates during dose dispensing. In addition, the piston rod may be coupled to a drive member for driving the piston rod. The drive member is preferably permanently rotationally constrained to the piston rod. Thus, the drive member preferably does not rotate during dose setting and rotates during dose dispensing.

To prevent unintended movement of the drive member during dose setting, it may be rotationally constrained to the housing via a clutch, for example engaging teeth, thus preventing rotation of the drive member as long as the clutch is engaged. Axial movement of the drive member may be used to engage and disengage this clutch. In other words, during dose setting the drive member may be in a first axial position, preferably a proximal position, relative to the housing and during dose dispensing the drive member may be in a second, different axial position, preferably a distal position, relative to the housing, wherein the axial movement of the drive member effects rotationally coupling and decoupling the drive member to and from the housing.

Further, the injection device may comprise a clutch arranged between the drive member and the dose indicator. This clutch allows relative rotation of the drive member and the dose indicator during dose setting and rotationally constrains the drive member and the dose indicator during dose dispensing. Again, this clutch is preferably coupled and decoupled by the drive member travelling axially within the housing between a dose setting position and a dose dispensing position. This clutch may comprise a clutch plate with a first ring of clutch teeth engaging corresponding teeth of the drive member and a second series of clutch teeth engaging corresponding teeth of the dose indicator. In the dose setting position at least one of the corresponding teeth are allowed to bump over each other, wherein in the dose dispensing position the teeth are firmly pressed against each other, thus, rotationally constraining the drive member to the dose indicator.

Preferably, this clutch between the dose indicator and the drive member comprises ratchet teeth, for example a first series of ratchet teeth on the drive member and a second series of ratchet teeth on a clutch plate interposed between the drive member and the dose indicator, which ratchet teeth are designed such that the resistance for overcoming the ratchet teeth is larger in a first rotational direction compared with a second, opposite direction. For example, the torsion spring may be arranged acting between the housing and the dose indicator.

Thus, the clutch with the ratchet teeth has to prevent the dose indicator from rotating back by the torque applied by the torsion spring. The torque necessary to overhaul the ratchet in the first (e.g. anti clockwise) direction may be a function of the axial load applied by a return spring, the ramp angle of the ratchet in the first direction, the friction coefficient between the mating surfaces and the mean radius of the ratchet features. The torque necessary to overhaul the ratchet must be greater than the torque applied to the dose indicator (and hence clutch plate) by the torsion spring. The ratchet ramp angle is therefore increased in the first direction to ensure this is the case whilst ensuring the torque required to rotate the dial in the second direction is as low as possible.

Further, with the mechanism in a state in which a dose has been selected, the user is preferably able to deselect any number of increments from this dose. Deselecting a dose may be achieved by the user rotating the dial grip anti-clockwise. The torque applied to the dial grip by the user is sufficient, when combined with the torque applied by the torsion spring, to overhaul the ratchet between the clutch plate and drive member in the anti-clockwise direction. When the ratchet is overhauled, anti-clockwise rotation occurs in the dose indicator (via the clutch plate), which unwinds the torsion spring.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to avoid overdosage. Preferably, the limits for the minimum dose and the maximum dose are provided by hard stop features. The limiter mechanism may comprise a first rotational stop on the dose indicator and a first counter stop on the gauge element, which abut in the minimum dose (zero) position, and a second rotational stop on the dose indicator and a second counter stop on the gauge element, which abut in the maximum dose position.

To prevent an underdosage or a malfunction, the drug delivery device may comprise a last dose protection mechanism for preventing the setting of a dose, which exceeds the amount of liquid left in a cartridge. The last dose protection mechanism may comprise a nut member located interposed between the drive member and the dose indicator. In a preferred embodiment, the dose indicator rotates during dose setting and during dose dispensing, whereas the drive member only rotates during dose dispensing together with the dose indicator. Thus, in this embodiment, the nut member will only move during dose setting (or dose cancelling) and will remain stationary with respect to these components during dose dispensing. Preferably, the nut member is threaded to the drive member and splined to the dose indicator. As an alternative, the nut member may be threaded to the dose indicator and may be splined to the drive member. The nut member may be a full nut or a part thereof, e.g. a half nut.

In an alternative embodiment, the last dose nut may be provided between a dial sleeve, which is rotatable only during dose setting, and a clicker sleeve, which is permanently rotationally constrained to the housing. Again, the nut member will only move during dose setting (or dose cancelling) and will remain stationary with respect to these components during dose dispensing.

The injection device may comprise at least one clicker mechanism for generating a tactile and/or audible feedback. Preferably, the clicker mechanism signifies the end of dose dispensing. In some embodiments, the device comprises at least a first clicker producing an audible and/or tactile first feedback during dose setting and/or dose dispensing and a second clicker producing an audible and/or tactile second feedback, distinct from the first feedback, during dose dispensing only when the device reaches its minimum dose (zero) position. The injection device may have different clickers active during dose setting and during dose dispensing. Preferably, the second clicker comprises a flexible arm provided on the dose indicator, which is displaced in a radial direction by a flange or protrusion of the drive member, and a radially inwardly protruding section of the gauge element, which passes over the flexible arm upon relative rotation of the dose indicator and the gauge element.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phed-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys) 6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha$, $\delta$, $\epsilon$, $\gamma$, and $\mu$. The type of heavy chain present defines the isotype of antihousing; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region (CH) and the variable region (VH). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antihousing contains two light chains that are always identical; only one type of light chain, $\kappa$ or $\lambda$, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The disclosure relates to a medical device that can be operated to deliver variable, user-selectable, doses of medicament from a cartridge, via a needle. In a preferred embodiment, the device is disposable. It is delivered to the user in a fully assembled condition ready for first use.

A dose may be set by rotating a dial grip located at the end of the housing. Delivery of a dose is initiated by pressing the end of the dial grip and displacing the dial grip axially in the distal direction. Dose delivery will continue while the dial grip remains depressed, until the complete set dose has been delivered. The mechanism provides audible, visual and tactile feedback both on the setting and delivery of each dose.

The mechanism contains a helical torsion spring to store energy, which is charged during setting of the dose, by the action of the user rotating the dial grip. The spring energy is stored until the mechanism is triggered for dispense at which point the energy stored is used to deliver the medicament from the cartridge to the user. Any dose size can be selected between zero and a pre-defined maximum, in increments to suit the medicament and user profile. The mechanism permits cancelling of a dose without any medicament being dispensed by rotation of the dial grip in the opposing direction to when selecting a dose.

BRIEF DESCRIPTION OF THE FIGURES

A non-limiting, exemplary embodiment will now be described with reference to the accompanying drawings, in which:

FIG. 8 shows an enlarged cut away view of a detail of the device of FIG. 1;

FIG. 9 shows an enlarged perspective view of a detail of the device of FIG. 1;

FIG. 10 shows an enlarged perspective view of a detail of the device of FIG. 1;

FIG. 11 shows an enlarged perspective view of a detail of the device of FIG. 1;

DETAILED DESCRIPTION

Figure 1:
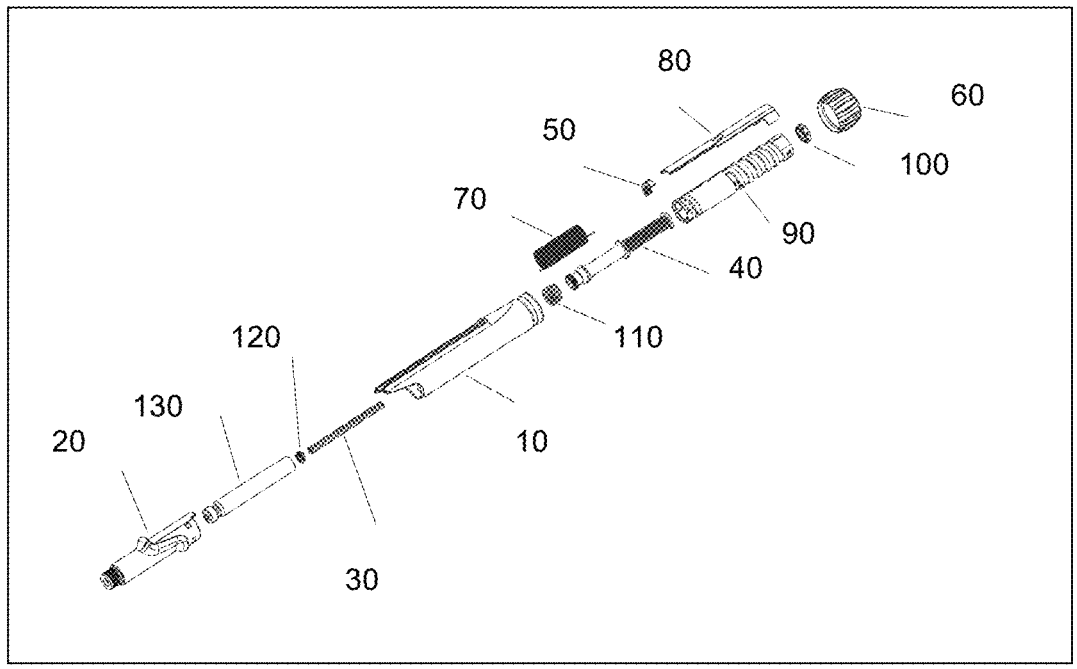
FIG. 1 shows an exploded view of the components of an injection device in accordance with a first embodiment.
Figure 2:
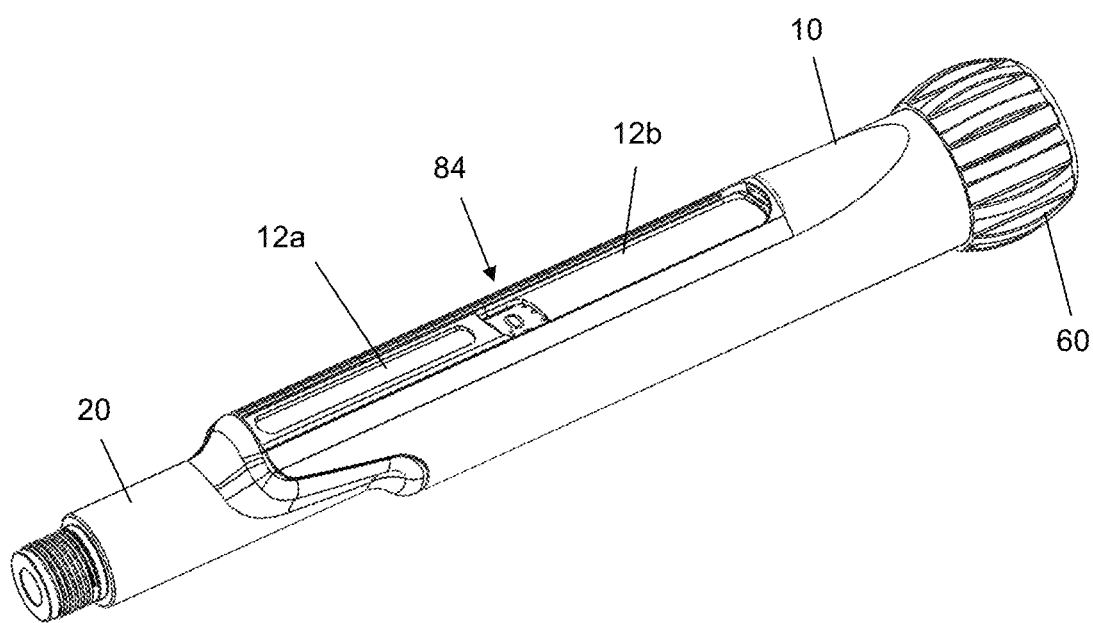
FIG. 2 shows a perspective view of the device of FIG. 1.
Figure 3:
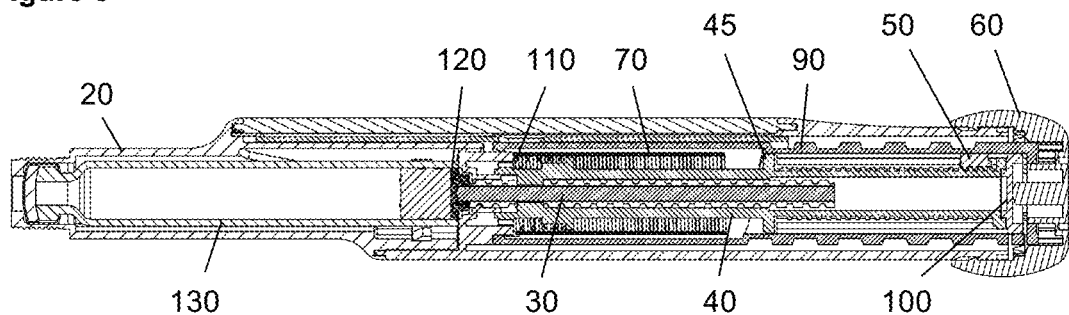
FIG. 3 shows a sectional view of the device of FIG. 1.

FIG. 2 shows a drug delivery device in the form of an injection pen. The device has a distal end (lower end in FIG. 2) and a proximal end (upper end in FIG. 2). The component parts of the drug delivery device are shown in FIG. 1. All components are located concentrically about a common principal axis of the mechanism. The drug delivery device comprises a body or housing 10, a cartridge holder 20, a lead screw (piston rod) 30, a drive member 40, a nut 50, a dial grip 60, a torsion spring 70, a gauge element 80, a dose indicator (number sleeve) 90, a clutch plate 100, a return spring 110, a bearing 120 and a cartridge 130. A needle arrangement (not shown) with a needle hub and a needle cover may be provided as additional components, which can be exchanged as explained above.

The housing 10 is a generally tubular component which provides location for the liquid medication cartridge 130 and the cartridge holder 20. A ring of teeth 11 provide an interface to prevent rotation of the drive member 40 when in its proximal dose setting position. Further the gauge element 80 is guided in housing 10 in an axially displaceable but rotationally fixed manner. Two slots 12*a*, 12*b* are provided extending in the longitudinal direction of the housing. Through slot 12*b* the dose number on the dose indicator 90 can be viewed. A groove-like feature 13 on the external housing surface axially retains the dial grip 60. The housing 10 has an inwardly protruding web with a thread 14 receiving the piston rod 30. Teeth 15 are provided at the proximal end of housing 10 for interaction with dial grip 60 during dose dispense. In a preferred embodiment, there is only one window in the housing, showing both the gauge area that covers and reveals the contrast element and also showing the dose number.

The cartridge holder 20 receives cartridge 130 and is permanently attached to housing 10. A slot or window (not shown) may be provided through which the cartridge 130 can be viewed.

The piston rod 30 has an external thread 31 and is rotationally constrained to the drive member 40 via a splined interface. When rotated, the piston rod 30 is forced to move axially relative to the housing 10, through its threaded interface 14, 31 with the housing 10. The bearing 120 is axially constrained to the piston rod 30 and acts on the bung within the liquid medicament cartridge 130.

The drive member 40 is a tubular element, which extends from the interface with the dose indicator 90 (via the clutch plate 100) down to a splined tooth interface 41, 11 with the housing 10. This provides rotational constraint to the drive member 40 during dose setting. When the dial grip 60 is pressed, these spline teeth 41 are disengaged allowing the drive member 40 to rotate. At its proximal end, there are teeth 42 for engaging corresponding ratchet teeth of the clutch plate 100. A proximal portion of the drive member 40 is provided with an outer thread 43 forming a helical path guiding nut 50. Two flanges are located on either end of the threaded portion with a rotational hard stop 44 located at the distal end of the threaded portion. The flange 45 which is located near the hard stop 44 may have a tapered face for an end of dose clicker.

The nut 50 is located between the dose indicator 90 and the drive member 40. It is rotationally constrained to the dose indicator 90, via a splined interface indicated by splines 51 shown in FIG. 9. It moves along the helical path 43 relative to the drive member 40, via a threaded interface, when relative rotation occurs between the dose indicator 90 and drive member 40 (during dialing only).

The dial grip 60 is splined to the dose indicator 90 by teeth 61 when in the dialing condition. This spline interface is disconnected when the dial grip 60 is pressed to trigger a dispense. The dial grip 60 is radially constrained to the housing 10 by a snap fit engaging groove 13 and allowed to move axially by a small amount—this equals the dial grip 60 axial travel required to trigger the mechanism. When depressed, the dial grip 60 is rotationally constrained to the housing 10 via a splined engagement formed by teeth 62 and teeth 15 at the proximal end of the housing 10. Further, a ring of radial ratchet features 63 is provided interacting with a compliant clicker arm 91 of dose indicator 90.

The torsion spring 70 is attached at one end to the housing 10 and at the other end to the dose indicator 90. The torsion spring 70 is pre-wound upon assembly, such that it applies a torque to the dose indicator 90 when the mechanism is at zero units dialed. The action of rotating the dial grip 60, to set a dose, rotates the dose indicator 90 relative to the housing 10, and charges the torsion spring 70.

Figure 5:
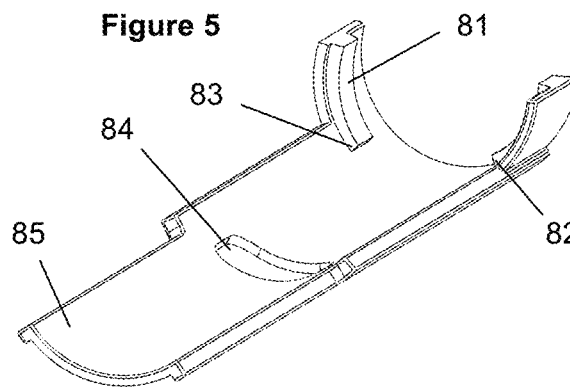
FIG. 5 shows an enlarged view of a detail of the device of FIG. 1.

The gauge element 80 is constrained to prevent rotation but allow translation relative to the housing 10 via a splined interface. As shown in FIG. 5, the gauge element 80 has helical features 81 on its inner surface which engage with the helical thread 92 cut in the dose indicator 90 such that rotation of the dose indicator 90 causes axial translation of the gauge element 80. These helical features 81 on the gauge element 80 also create stop abutments 82, 83 against the end of the helical cut in the dose indicator 90 to limit the minimum and maximum dose that can be set. There is an aperture 84 in the gauge element 80 through which a small portion of the dose indicator 90 can be viewed. In a preferred embodiment, there is only one portion of thread on the gauge instead of helical features 81.

Figure 6:
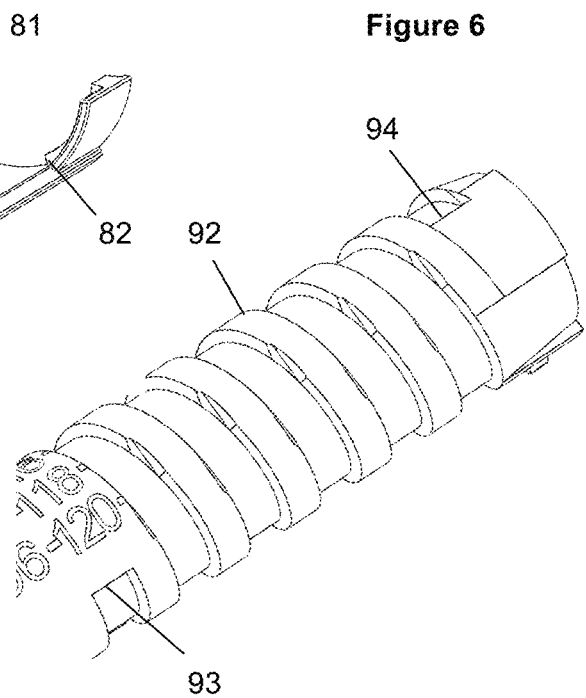
FIG. 6 shows an enlarged view of a detail of the device of FIG. 1.
Figure 7A:
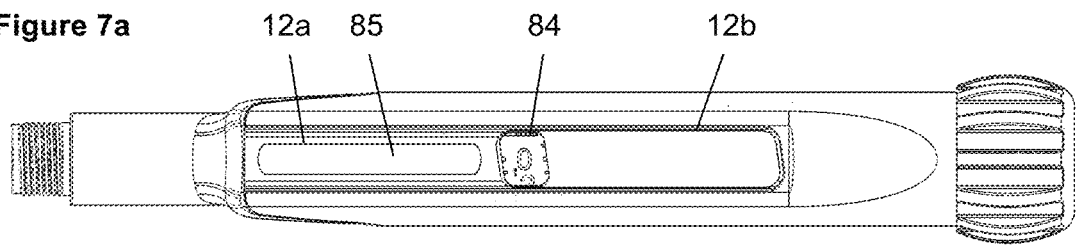
FIG. 7*a* shows a perspective view of the device of FIG. 1 with a dose of 0 units set.
Figure 7B:
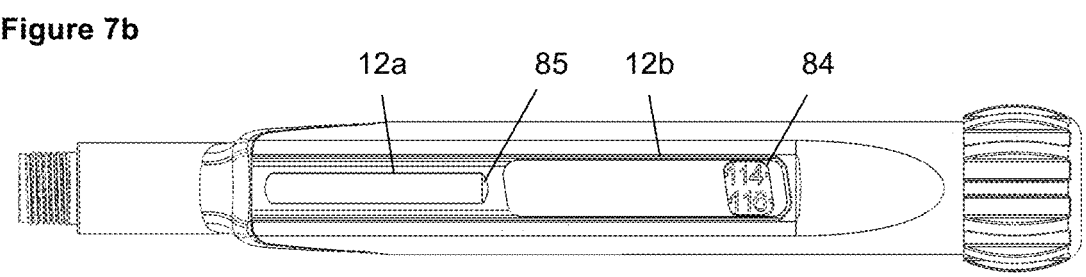
FIG. 7*b* shows a perspective view of the device of FIG. 1 with a dose of 115 units set.

The dose indicator 90, which is shown in FIG. 6, is constrained, via features at its distal end, to the housing 10 to allow rotation but not axial translation. The dose indicator 90 is marked with a sequence of numbers, which are visible through the gauge element 80 and the slot 12*b* in the housing 10, to denote the dialed dose of medicament. The helical thread 92 has rotational hard stops 93, 94 at the respective ends forming a zero dose abutment and a maximum dose abutment for the helical features 81 of the gauge element 80. In addition to clicker arm 91, a further clicker arm 95 is provided for an end of dose click. In a preferred embodiment, the dose indicator is split into two parts for moulding reasons, but they are rigidly fixed together during assembly so function as a single part.

The clutch plate 100 is splined to the dose indicator 90. It is also coupled to the drive member 40 via a ratchet interface, which occurs on an axial abutment. The ratchet provides a detented position between the dose indicator 90 and drive member 40 corresponding to each dose increment, and engages different ramped tooth angles during clockwise and anti-clockwise relative rotation.

The return spring 110 acts against the drive member 40 to bias the spline teeth 41 into engagement with the housing 10. The axial position of the drive member 40, clutch plate 100 and dial grip 60 is defined by the action of the return spring 110, which applies a biasing force on the drive member 40 in the proximal direction. In the "at rest" position, this ensures that the dial grip 60 splines are engaged with the dose indicator 90 and that the drive member 40 teeth are engaged with the housing 10.

A removable Cap fits over the cartridge holder 20 and is retained via clip features—this is not shown in the figures.

Figure 4A:
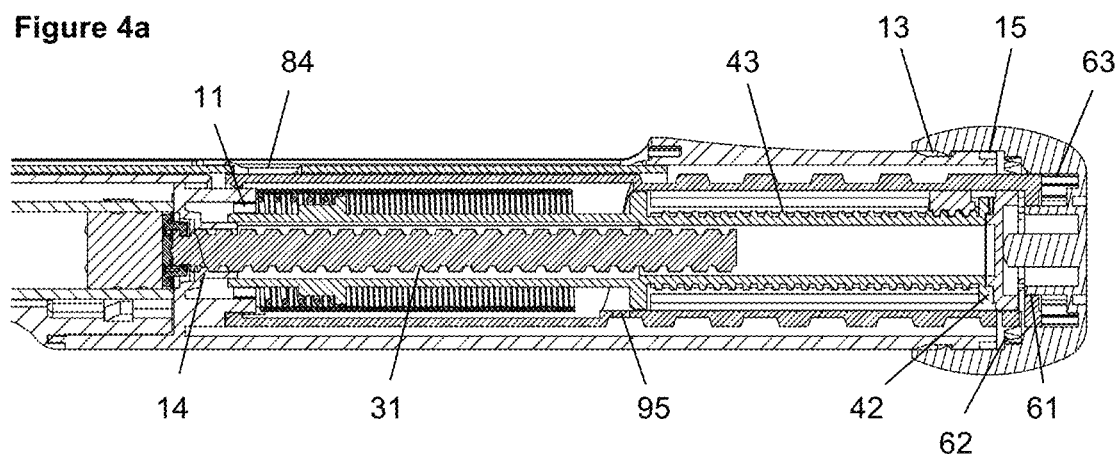
FIG. 4*a* shows an enlarged sectional view of a detail of the device of FIG. 1 in the dose setting position.
Figure 4B:
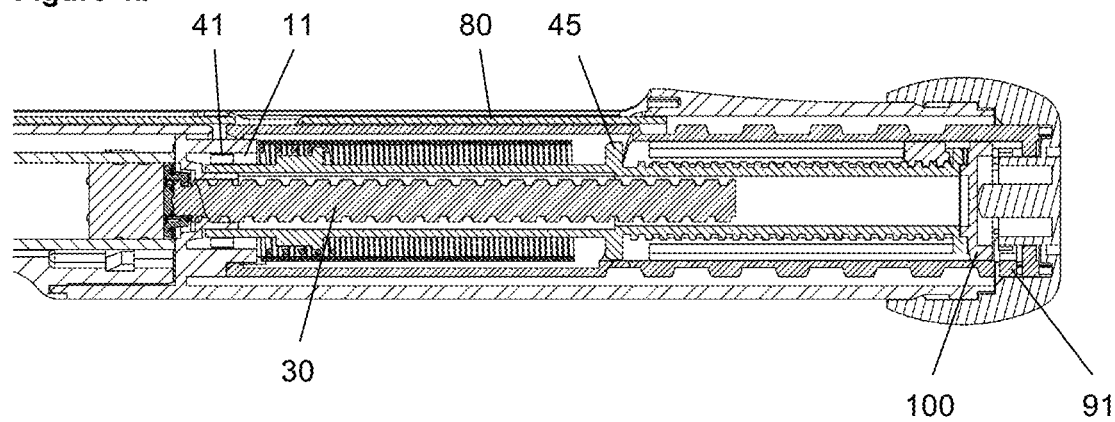
FIG. 4*b* shows the enlarged sectional view of the detail of FIG. 4*a* in the dose dispensing position.

With the device in the "at rest" condition, the dose indicator 90 is positioned with its zero dose abutment 93 against the zero dose abutment 83 of the gauge element 80 and the dial grip 60 is not depressed, i.e. in the position shown in FIG. 4*a*. Dose marking '0' on the dose indicator 90 is visible through the window 12*b* of the housing 10 and window 84 of the gauge element 80. The torsion spring 70, which has a number of pre-wound turns applied to it during assembly of the device, applies a torque to the dose indicator 90 and is prevented from rotating by the zero dose abutment.

The user selects a variable dose of liquid medicament by rotating the dial grip 60 clockwise, which generates an identical rotation in the dose indicator 90. Rotation of the dose indicator 90 causes charging of the torsion spring 70, increasing the energy stored within it. As the dose indicator 90 rotates, the gauge element 80 translates axially due to its threaded engagement thereby showing the value of the dialed dose in window 84. The gauge element 80 has flanges either side of the window area which cover the numbers printed on the dose indicator 90 adjacent to the dialed dose to ensure only the set dose number is made visible to the user. In a preferred alternative embodiment, rotation of the dial grip causes an identical rotation of the dose indicator during dialing, via splined interfaces between the dial grip and dose button and between the dose button and dose indicator.

One specific element of this mechanism is inclusion of a visual feedback feature in addition to the discrete dose number display typical on devices of this type. The distal end 85 of the gauge window creates a sliding scale through slot 12*a* in the housing 10. As a dose is set, by the user, the gauge element 80 translates axially, the distance moved proportional to the magnitude of the dose set. This feature gives clear feedback to the user regarding the approximate size of the dose set. The dispense speed of a spring driven auto-injector mechanism may be higher than for a manual injector device, so it may not be possible to read the numerical dose display during dispense. The gauge feature provides feedback to the user during dispense regarding dispense progress without the need to read the dose number itself.

The gauge display may be formed by an opaque sliding element, namely the distal portion 85, revealing a contrasting coloured component underneath, for example a portion of the housing 10, of the cartridge holder 20 or of the dose indicator 90. Alternatively, the concealed component may be printed with coarse dose numbers or other indices to provide more precise resolution. In addition, the gauge display simulates a syringe action during dose set and dispense.

The mechanism utilises a dial grip 60 with an increased diameter relative to the housing 10 which aids dialing although this is not a requirement of the mechanism. This feature is particularly important for an auto-injector mechanism where a power supply is charged during dose setting and the torque required to turn the dial grip 60 may be higher than for a non-auto injector device.

The drive member 40 is prevented from rotating as the dose is set and the dose indicator 90 rotated, due to the engagement of its splined teeth 41 with teeth 11 in the housing 10 as shown in FIG. 8. Relative rotation must therefore occur between the clutch plate 100 and drive member 40 via the ratchet interface 42.

The user torque required to rotate the dial grip 60 in the dose set direction (e.g. clockwise) is a sum of the torque required to wind up the torsion spring 70, and the torque required to overhaul the ratchet feature 42. The return spring 110 is designed to provide an axial force to the ratchet feature and to bias the clutch plate 100 onto the drive member 40. This axial load acts to maintain the ratchet teeth 42 engagement of the clutch plate 100 and drive member 40. The torque required to overhaul the ratchet in the dose set direction is a function of the axial load applied by the return spring 110, the ramp angle of the ratchet in the dose set direction, the friction coefficient between the mating surfaces and the mean radius of the ratchet features.

As the user rotates the dial grip 60 sufficiently to increment the mechanism by 1 increment, the dose indicator 90 rotates relative to the drive member 40 by 1 ratchet tooth 42. At this point the ratchet teeth re-engage into the next detented position. An audible click is generated by the ratchet re-engagement, and tactile feedback is given by the change in torque input required.

Relative rotation of the dose indicator 90 and the drive member 40 also causes the nut 50 to travel along its threaded path 43, towards its last dose abutment 44 on the drive member 40. The nut 50 is designed as a partial nut to aid assembly and the dose indicator 90 provides radial constraint to prevent the nut 50 disengaging the drive member thread 43. The position of the nut 50 is indicative of the sum of the actually set and the already dispensed doses. It is used as a last dose mechanism preventing setting of a dose which exceeds the amount of medicament remaining in the cartridge. As a preferred alternative, the nut 50 could also be a complete nut.

With no user torque applied to the dial grip 60, the dose indicator 90 is now prevented from rotating back by the torque applied by the torsion spring 70, solely by the ratchet 42 engagement between the clutch plate 100 and the drive member 40. The torque necessary to overhaul the ratchet in the dose-cancel direction is a function of the axial load applied by the return spring 110, the ramp angle of the ratchet in the dose-cancel direction, the friction coefficient between the mating surfaces and the mean radius of the ratchet features. The torque necessary to overhaul the ratchet must be greater than the torque applied to the dose indicator 90 (and hence clutch plate 100) by the torsion spring 70. The ratchet ramp angle is therefore increased in the dose-cancel direction to ensure this is the case whilst ensuring the dial-up torque is as low as possible.

The user may now choose to increase the selected dose by continuing to rotate the dial grip 60 in the clockwise direction. The process of overhauling the ratchet interfaces 42 between the dose indicator 90 and drive member 40 is repeated for each dose increment. Additional energy is stored within the torsion spring 70 for each dose increment and audible and tactile feedback is provided for each increment dialed by the re-engagement of the ratchet teeth 42. The torque required to rotate the dial grip 60 increases as the torque required to wind up the torsion spring 70 increases. The torque required to overhaul the ratchet in the anti-clockwise direction must therefore be greater than the torque applied to the dose indicator 90 by the torsion spring 70 when the maximum dose has been reached.

If the user continues to increase the selected dose until the maximum dose limit 82, 94 is reached, the dose indicator 90 engages with its maximum dose abutment on the gauge element 80. This prevents further rotation of the dose indicator 90, clutch plate 100 and dial grip 60.

Depending on how many increments have already been delivered by the mechanism, during selection of a dose, the nut 50 may contact its last dose abutment 44 with the drive member 40. The abutment prevents further relative rotation between the dose indicator 90 and the drive member 40, and therefore limits the dose that can be selected. The position of the nut 50 is determined by the total number of relative rotations between the dose indicator 90 and drive member 40, which have occurred each time the user sets a dose.

With the mechanism in a state in which a dose has been selected, the user is able to deselect any number of increments from this dose. Deselecting a dose is achieved by the user rotating the dial grip 60 anti-clockwise. The torque applied to the dial grip 60 by the user is sufficient, when combined with the torque applied by the torsion spring 70, to overhaul the ratchet 42 between the clutch plate 100 and drive member 40 in the dose-cancel direction. When the ratchet is overhauled, rotation in the dose-cancel direction occurs in the dose indicator 90 (via the clutch plate 100), which returns the dose indicator 90 towards the zero dose position, and unwinds the torsion spring 70. The relative rotation between the dose indicator 90 and drive member 40 causes the nut 50 to return along its helical path 43, away from the last dose abutment.

With the mechanism in a state in which a dose has been selected, the user is able to activate the mechanism to commence delivery of a dose. Delivery of a dose is initiated by the user depressing the dial grip 60 axially. As can be taken from a comparison of FIGS. 4a (showing the "at rest" state) and 4b (showing the device with dial grip 60 depressed), when the dial grip 60 is depressed, splines 61 between the dial grip 60 and the dose indicator 90 are disengaged, rotationally disconnecting the dial grip 60 from the delivery mechanism (so that the dial grip 60 does not rotate during dispense). In a preferred embodiment, the dial grip is disconnected from the drive member during dispense, when splines between the dose button and housing are engaged and splines between the dose button and dose indicator are disengaged.

The dial grip 60 acts on the drive member 40, via the clutch plate 100, which travels axially and disconnects its splined engagement 11, 41 with the housing 10. The drive member 40 can now rotate and is driven by the torsion spring 70 via the dose indicator 90, and clutch plate 100. Rotation of the drive member 40 causes the piston rod 30 to rotate due to their splined engagement, and the piston rod 30 then advances due to its threaded engagement to the housing 10. The dose indicator 90 rotation also causes the gauge element 80 to traverse axially back to its zero position whereby the zero dose abutment 83, 93 stops the mechanism.

Audible feedback during dose dispense is provided via compliant cantilever clicker arm 91 integrated into the proximal end of the dose indicator 90 which is shown in FIG. 10. This arm 91 interfaces radially with ratchet features 63 on the inner surface of the dial grip 60 (FIG. 11), whereby the ratchet tooth spacing corresponds to the dose indicator 90 rotation required for a single increment dispense. During dispense, as the dose indicator 90 rotates and the dial grip 60 is rotationally coupled to the housing 10, the ratchet features 63 engage with the clicker arm 91 to produce an audible click with each dose increment delivered.

Delivery of a dose continues via the mechanical interactions described above while the user continues to depress the dial grip 60. If the user releases the dial grip 60, the return spring 110 returns the dial grip 60 to its "at rest" position via the drive member 40 and clutch plate 100, the drive member 40 becomes rotationally constrained and delivery of a dose is halted.

During delivery of a dose, the drive member 40 and dose indicator 90 rotate together, so that no relative motion in the nut 50 occurs. The nut 50 therefore travels axially on the drive member 40 during dialing only.

Once the delivery of a dose is stopped, by the dose indicator 90 returning to the zero dose abutment 83, 93, the user may release the dial grip 60, which will re-engage the drive member 40 spline teeth 41 with the housing 10. The mechanism is now returned to the "at rest" condition.

It is possible to angle the spline teeth 11, 41 on either the drive member 40 or housing 10 or both so that when the dial grip 60 is released the re-engagement of the spline teeth 11, 41 fractionally 'backwinds' the drive member 40 thereby removing the engagement of the dose indicator 90 to the gauge element 80 zero dose stop abutment 83. This compensates for the effect of clearances in the mechanism (for example due to tolerances) which could otherwise lead to slight advancement of the piston rod 30 and medicament dispense when the device is dialed for the subsequent dose (due to the dose indicator 90 zero dose stop no longer restraining the mechanism and instead the restraint returning to the splines 41, 11 between the drive member 40 and housing 10).

Figure 12A:
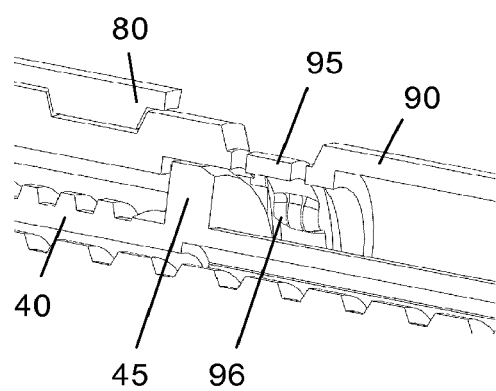
FIG. 12*a-d* show an enlarged cut away view of a detail of the device of FIG. 1 in different states of the device.

At the end of dose, additional audible feedback is provided in the form of a "click", distinct from the "clicks" provided during dispense, to inform the user that the device has returned to its zero position via the interaction of three components, the dose indicator 90, gauge element 80 and drive member 40, in more detail the flange 45, a stepped guiding face formed by helical features 81 and the flexible arm 95. This embodiment allows feedback to only be created at the end of dose delivery and not created if the device is dialed back to, or away from, the zero position. FIG. 12a shows the position of the features when the device is in the dose set condition. It can be seen that flange 45 of the drive member 40 does not contact the flexible arm 95 of the dose indicator 90 when the dial grip 60 is in the "at rest" condition and, therefore, during dialing the flexible arm 95 is not deflected.

Figure 12B:
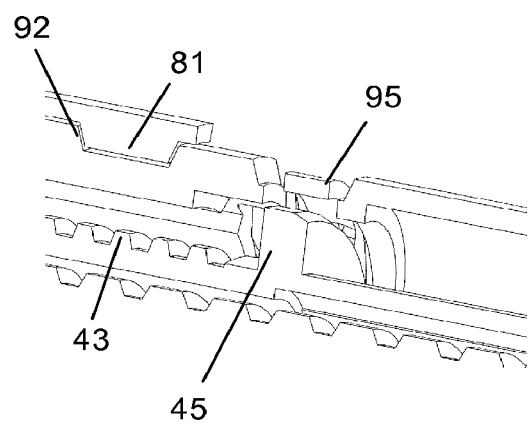
Figure 12C:
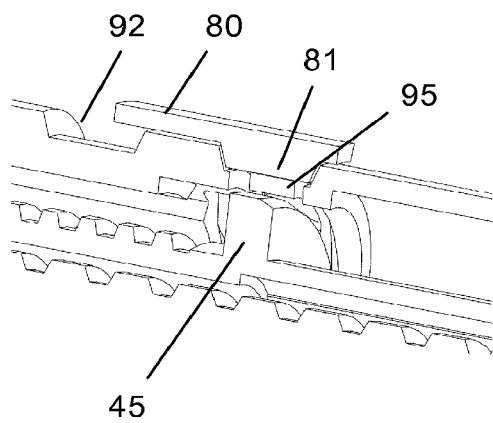
Figure 12D:
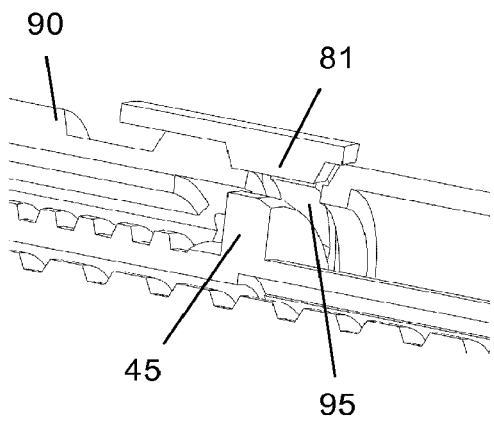

During dose delivery, dial grip 60 is depressed to initiate dose dispense and the drive member 40 is translated axially, whereby the flange 45 on the drive member 40 axially aligns with a protrusion 96 on the flexible arm 95 of dose indicator 90. This forces the flexible arm to deflect radially outwards as shown in FIG. 12b. The tip of the flexible arm moves into the space on the outside of the dose indicator 90 left whilst gauge element 80 is not nearing the zero unit position. FIG. 12c shows the device with approximately 1 unit remaining to dispense. The flexible arm 95 is charged as the gauge element 80 with its helical feature follows dose indicator 90 thread and contacts with the helical feature 81 of the gauge element 80, which forms a stepped guiding face, the tip of flexible arm 95. The tip of the flexible arm is thereby deflected radially inwards, whilst the protrusion 96 on the inner surface is restrained from radial deflection via the flange 45 on the drive member 40. The end of dose click is created (FIG. 12d) as the tip of the charged flexible arm 95 is released from the underside of the stepped guiding face (helical feature 81) on gauge element 80 and the dose indicator 90 rotates and tip of flexible arm 95 passes the edge of helical feature 81 (stepped guiding face). Following release of the dial grip 60, the mechanism returns to the condition shown in FIG. 12a, so no flexible elements remain stressed in the "at rest" condition.

Summarizing, the mechanism has no dial extension, and a low actuation force trigger. The dial grip 60 is rotationally locked during dispense and shaped to make dialing easier. The gauge feature provides qualitative feedback to the user on the progress of the dose. All of which combine to provide a significant ergonomic benefit to the user.

Figure 13:
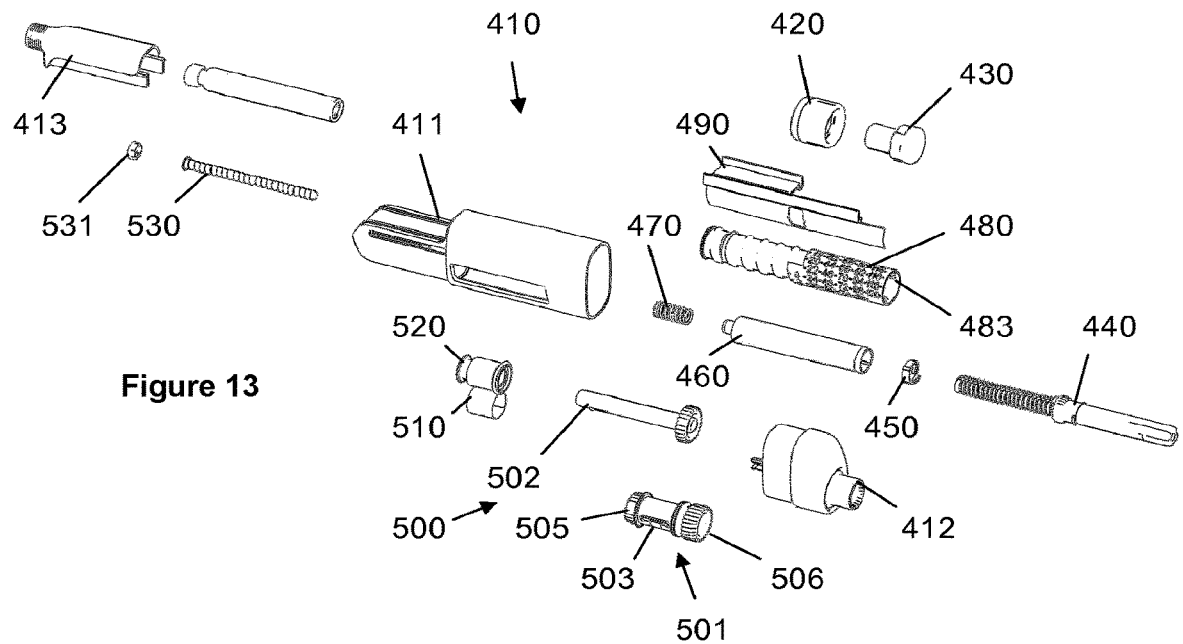
FIG. 13 shows an exploded view of the components of an injection device in accordance with a second embodiment.
Figure 14:
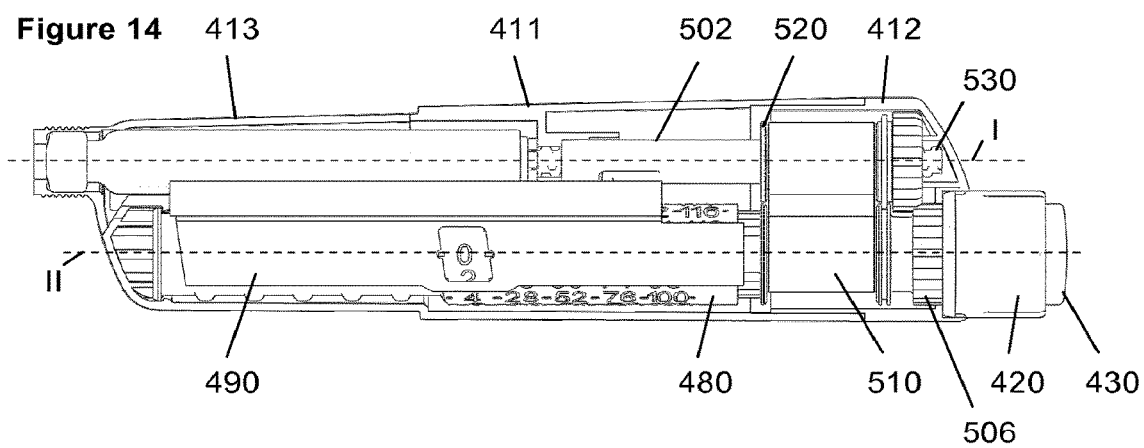
FIG. 14 shows a partially cut away side view of the device of FIG. 13.

An alternative second embodiment of an injection device 1 is shown in FIG. 13 in an exploded view. The injection device comprises 19 components, excluding the liquid medicament cartridge. In more detail, the device comprises a housing 410, which includes a main housing 411, a proximal cap 412 and a cartridge holder 413, a dial grip 420, a dispense button 430, a dial tube 440, a last dose nut 450, a sleeve-like clicker 460, a dispense spring 470, a dose indicator (dial sleeve) 480, a sliding gauge 490, a drive member 500 including a drive sleeve 501 and a drive tube 502, a motor spring 510, a storage spool 520, a piston rod (lead screw) 530 with a bearing 531, a lens (not shown) and a cap (not shown). Most of the components are located concentrically about one of two principle axes I and II of the mechanism as shown in FIG. 14.

The piston rod 530 is located within the housing 510. The drive member 500 is permanently coupled to the piston rod 530 and the drive member 500 is axially movable between a dose setting position, in which the drive member 500 is rotationally constrained to the housing 410, and a dose dispensing position, in which the drive member 500 is rotationally de-coupled from the housing 410. The power reservoir 510 for driving the drive member 500 comprising a reverse wound flat spiral spring as a power reservoir having a first end attached to the first spool 520 and a second end attached to a second spool, which is axially and rotationally constrained to drive member 500. For example, the second spool is an integral part of drive sleeve 501. In the embodiment shown in the Figures, the second end of the spring 510 comprises a portion of reduced width and a free end portion having an increased width compared with the portion of reduced width, wherein the drive member 500, in more detail drive sleeve 501, comprises a cylindrical spool portion having an axial slot 503 and an adjacent narrow recess.

Preferably, the dose indicator 480 is axially constrained to the housing 410 and rotates during dose setting relative to the housing in either a first direction (increasing a dose) or a second opposite direction (decreasing a dose) and it rotates during dose dispensing relative to the housing in the second opposite direction. The gauge element 490 is at least partly interposed between the housing 410 and the dose indicator 480 and at least partly visible through at least one aperture or window of the housing 410. Further, the gauge element 490 is axially guided within the housing 410 and in threaded engagement with the dose indicator 480 such that rotation of the dose indicator 480 causes an axial displacement of the gauge element 490. The housing 410 has an aperture or window and the gauge element 490 has a further aperture or window, which is positioned with respect to the aperture or window of the housing such that at least a part of the dose indicator 480 is visible through the apertures or windows.

In particular, the apertures may be located on the main housing 411 in a location which is visible to the user during dispense of a dose. This may be close to the distal end of the device. Particularly this may be a location in which the number display of the dose indicator 480 could not feasibly be located. There may also be a plurality of gauge apertures. In particular there may be two gauge apertures, located on opposite sides of the device This increases the visibility of the analog gauge feature for users with a preference for left handed operation, or those users with a preference to hold the device with an alternative grip. The analog gauge is particularly beneficial as an indicator of the dose position of the device during dispense of a dose. During dispense of a dose the number digit display may be changing too quickly for individual dose position markings to be legible. It may therefore be difficult for the user to understand the rate at which the dose is being dispensed, and the amount of medicament still to be dispensed. The axial motion of the analog gauge, which increasingly covers a further surface as a dose is dispensed, gives a simple visible indicator of the dispense rate and the amount of medicament still be to dispensed during the dispense event.

The injection device comprises a limiter mechanism defining a maximum settable dose and a minimum settable dose. The limiter mechanism may comprise a first rotational stop on the dose indicator 480 and a first counter stop on the gauge element 490, which abut in the minimum dose (zero) position, and a second rotational stop on the dose indicator 480 and a second counter stop on the gauge element 490, which abut in the maximum dose position.

The dispense button 430 is axially displaceable and located surrounded by the dial grip 420 which is axially constrained to the housing 410. The clicker sleeve 460 is rotationally constrained to the housing 410 and is axially displaceable relative to the housing between a proximal dose setting position and a distal dose dispensing position. Further, the clicker sleeve 460 comprises teeth releasably engaging corresponding teeth of the dial sleeve 440 which is rotatable during dose setting. The dose indicator 480 may comprise a flexible clicker arm, which is displaceable by the clicker sleeve 460 in a first direction and only during dose dispensing when the device reaches its minimum dose (zero) position in a second, opposite direction by a protruding section of the gauge element 490.

The injection device may further comprise a last dose protection mechanism for preventing the setting of a dose, which exceeds the amount of liquid left in a cartridge. This last dose protection mechanism comprises the nut member 450 located interposed between the clicker sleeve 460 and the dial sleeve 440.

In the injection device the first spool 520 is located concentrically with the piston rod 530 on the first longitudinal axis I, and the second spool, i.e. the drive sleeve 501, is located on a second longitudinal axis II, wherein the first longitudinal axis I is parallel to and spaced from the second longitudinal axis II. As mentioned above, the drive member 500 may comprise the drive tube 502 which is rotatable about the first longitudinal axis I and the drive sleeve 501 which is rotatable about the second longitudinal axis II. The drive sleeve 501 is axially movable between the dose setting position, in which the drive sleeve 501 is rotationally constrained to the housing 410, and the dose dispensing position, in which the drive sleeve 501 is rotationally de-coupled from the housing 410. The drive tube 502 may be permanently rotationally coupled to the drive sleeve 501 or at least if the drive sleeve 501 is in its dose dispensing position.

A clutch 483, 505 is provided interposed between the dose indicator 480 and the drive member 500, wherein the clutch 483, 505 allows relative rotational movement between the dose indicator 480 and the drive member 500 during dose setting and prevents relative rotational movement between the dose indicator 480 and the drive member 500 during dose dispensing. As shown in FIG. 13, the clutch comprises a ring of teeth 505 on the distal side of drive sleeve 501 and inner splines 483 on the dose indicator. The drive sleeve 501 further has a ring of teeth 506 at its proximal end which mesh with corresponding teeth on the drive tube 502. In addition, teeth 506 couple the drive sleeve 501 rotationally to the housing in the (proximal) dose setting position of the drive sleeve 501.

The invention claimed is:

1. An injection device comprising:
   a housing;
   a dose indicator positioned within and axially constrained to the housing and rotatable with respect to the housing during dose setting and during dose dispensing;
   a gauge element at least partly interposed between the housing and the dose indicator, wherein the gauge element is axially guided within the housing and in threaded engagement with the dose indicator such that rotation of the dose indicator causes an axial displacement of the gauge element; and
   a contrast element comprising a first marking, wherein at least a region of the gauge element comprises a second marking, wherein at least one of the first marking or the second marking is visible through a first window or aperture in the housing depending on the axial position of the gauge element within the housing,
   wherein the gauge element does not protrude out of the housing during dose setting and does not protrude out of the housing during dose dispensing.

2. The injection device according to claim 1, wherein the contrast element is part of the housing.

3. The injection device according to claim 1, further comprising a cartridge holder for receiving a cartridge, wherein the gauge element is guided in the housing such that the gauge element at least in one of its axial positions during dose setting overlaps at least a part of the cartridge.

4. The injection device according to claim 1, further comprising a resilient member adapted to provide a force for ejecting a dose from the injection device.

5. The injection device according to claim 1, further comprising a piston rod, wherein the piston rod is rotationally fixed relative to the housing during dose setting and rotates relative to the housing during dose dispensing.

6. The injection device according to claim 1, further comprising a drive member, wherein the drive member is rotationally fixed relative to the housing during dose setting and rotates relative to the housing during dose dispensing.

7. The injection device according to claim 6, wherein the drive member is axially displaceable relative to the housing between a proximal dose setting position, wherein the drive member is rotationally constrained to the housing in the proximal dose setting position, and a distal dose dispensing position, wherein the drive member is rotationally decoupled from the housing in the distal dose dispensing position.

8. The injection device according to claim 6, further comprising a clutch arranged between the drive member and the dose indicator, wherein the clutch allows relative rotation of the drive member and the dose indicator during dose setting and rotationally constrains the drive member and the dose indicator during dose dispensing.

9. The injection device according claim 6, further comprising a last dose protection mechanism for preventing setting of a dose which exceeds an amount of liquid left in a cartridge, wherein the last dose protection mechanism comprises a nut member located between the drive member and the dose indicator or between a dial member and a clicker sleeve rotationally constrained to the housing.

10. The injection device according to claim 1, further comprising a limiter mechanism defining a maximum settable dose and a minimum settable dose, the limiter mechanism comprising a first rotational stop on the dose indicator and a first counter stop on the gauge element, the first rotational stop and the first counter stop abutting in the minimum dose position, and a second rotational stop on the dose indicator and a second counter stop on the gauge element, the second rotational stop and the second counter stop abutting in the maximum dose position.

11. The injection device according to claim 1, further comprising:
a first clicker producing at least one of an audible or tactile first feedback during at least one of dose setting or dose dispensing; and
a second clicker producing at least one of an audible or tactile second feedback, distinct from the first feedback, only during dose dispensing when the device reaches its minimum dose position.

12. The injection device according to claim 11, wherein the second clicker comprises a flexible arm provided on the dose indicator, wherein the flexible arm is displaceable in a radial direction by a flange or protrusion of a drive member or a clicker sleeve, and a radially inwardly protruding section of the gauge element, which passes over the flexible arm upon relative rotation of the dose indicator and the gauge element.

13. The injection device according to claim 1 further comprising a cartridge containing a medicament.

14. The injection device according to claim 1, further comprising a drive member that extends from an interface with the dose indicator to a splined tooth interface with the housing, wherein the splined tooth interface rotationally constrains the drive member during dose setting.

15. The injection device according to claim 14, further comprising a dial grip attached to an external surface of the housing, wherein pressing the dial grip disengages the drive member from the splined tooth interface allowing the drive member to rotate.

16. The injection device according to claim 14, further comprising a clutch plate, wherein the drive member extends from the interface with the dose indicator via the clutch plate.

17. The injection device according to claim 16, wherein the clutch plate comprises ratchet teeth that engage with teeth on a proximal end of the drive member.

18. The injection device according to claim 1, wherein the contrast element is part of the dose indicator.

\* \* \* \* \*

UNITED STATES PATENT AND TRADEMARK OFFICE
CERTIFICATE OF CORRECTION

PATENT NO. : 10,850,043 B2
APPLICATION NO. : 16/017794
DATED : December 1, 2020
INVENTOR(S) : William Marsh et al.

Page 1 of 1

It is certified that error appears in the above-identified patent and that said Letters Patent is hereby corrected as shown below:

In the Claims

Column 21, Line 10, Claim 9, delete "according" and insert -- according to --

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*